(12) United States Patent
Davies et al.

(10) Patent No.: US 9,572,658 B2
(45) Date of Patent: Feb. 21, 2017

(54) INTRAOCULAR LENS CARTRIDGE

(75) Inventors: Nathaniel Davies, Sussex (GB); Dario Vecchi, Sussex (GB)

(73) Assignee: Rayner Intraocular Lenses Limited, Buckinghamshire (GB)

( * ) Notice: Subject to any disclaimer, the term of this patent is extended or adjusted under 35 U.S.C. 154(b) by 826 days.

(21) Appl. No.: 13/321,752

(22) PCT Filed: May 14, 2010

(86) PCT No.: PCT/GB2010/000976
§ 371 (c)(1),
(2), (4) Date: Jan. 5, 2012

(87) PCT Pub. No.: WO2010/133825
PCT Pub. Date: Nov. 25, 2010

(65) Prior Publication Data
US 2012/0130390 A1  May 24, 2012

(30) Foreign Application Priority Data

May 22, 2009 (GB) .................................. 0908870.9

(51) Int. Cl.
*A61F 9/00* (2006.01)
*A61F 2/16* (2006.01)

(52) U.S. Cl.
CPC ........... *A61F 2/1678* (2013.01); *A61F 2/1691* (2013.01)

(58) Field of Classification Search
CPC ........ A61F 2/1691; A61F 2/1678; A61F 9/00; A61B 19/02
USPC ..................... 606/107, 169, 170, 171; 604/22
See application file for complete search history.

(56) References Cited

U.S. PATENT DOCUMENTS 5,499,987 A * 3/1996 Feingold ........................ 606/107

FOREIGN PATENT DOCUMENTS

| WO | 9958086 | 11/1999 |
|---|---|---|
| WO | 03045285 | 6/2003 |
| WO | 2004092780 | 10/2004 |

OTHER PUBLICATIONS

International Search Report for PCT/GB2010/000976 dated Aug. 20, 2010.

* cited by examiner

*Primary Examiner* — Victor Nguyen
(74) *Attorney, Agent, or Firm* — Andrus Intellectual Property Law, LLP

(57) ABSTRACT

A cartridge for storing and implanting an intraocular lens has a first part and a second part that are movable relative to one another from a storage configuration, in which interior surfaces of the first and second portions define a storage chamber for storing the IOL in an unfolded state, to an implanting configuration, in which the interior surfaces of the first and second portions together define a smooth-bored implanting chamber for retaining the IOL in a folded state. According to a first aspect, the first and second portions are hinged together, whereas according to a second aspect, the first and second portions are slidably interconnected.

6 Claims, 9 Drawing Sheets

INTRAOCULAR LENS CARTRIDGE

CROSS REFERENCE TO RELATED APPLICATION

The present application is the U.S. national stage application of International Application PCT/GB2010/000976, filed May 14, 2010, which international application was published on Nov. 25, 2010, as International Publication WO 2010/133825. The International Application claims priority of British Patent Application 0908870.9, filed May 22, 2009, the contents of which are incorporated herein by reference in their entireties.

FIELD OF THE INVENTION

The present invention relates to an intraocular lens cartridge for insertion into an injector for injecting an intraocular lens (IOL) contained within the cartridge into an eye of a patient.

BACKGROUND TO THE INVENTION

One of the operative treatments used to treat cataract is a method of removing a natural crystalline lens from an eye of a patient and then injecting an intraocular lens (IOL) in place of the natural crystalline lens.

The majority of first generation IOLs were manufactured from rigid PMMA and were implanted into the eye using forceps through large (5-6 mm) incisions. The large incision size increased the risk of infection and could lead to induced changes in the shape of the cornea and also potentially cause astigmatism of the eye after the operation. To prevent such disadvantages, a next generation of foldable IOLs was developed that could be introduced into the eye through a reduced incision size (2-4 mm) using an injector.

IOLs typically comprise a lens portion and a pair of resilient haptics extending outwardly from opposite sides of the periphery of the lens portion. The haptics aid in locating the IOL in a correct position in the eye and in maintaining the IOL in that correct position.

To inject the IOL, the following steps are usually performed: first making an incision in the eye; fragmenting and aspirating a clouded natural crystalline lens through the incision; and then injecting the IOL into the eye through the incision to implant it in place of the natural crystalline lens.

A first generation of injectors typically consisted of reusable titanium bodies fitted with disposable plastic cartridges, those cartridges being loaded with a foldable IOL at the point of use.

With reference to FIGS. 1a and 1b, the next generation of injectors 10 were plastic, disposable, single-use injectors. These often had cartridges 20 that were integral with the injector bodies 12, the IOL 50 being inserted at the point of use as in the previous injectors mentioned above. It is also known for the cartridge 20 to be a separate element, removably fitted into a loading bay of the injector 10. The foldable IOL 50 in the cartridge 20 is positioned so as to be aligned with a bore 14 in the injector 10 containing a plunger 16. A relatively narrow end portion 16' of the plunger engages the IOL 50 to urge the IOL toward the tip 18 of the injector. In some cartridges 20, the IOL 50 is held within the injector 10 and engaged by the plunger 16 in an unfolded state, in which case the tip 18 of the injector 10 will be tapered so as to fold the IOL into a smaller shape as it is pushed toward and through the tip 18 by the plunger 16. In other cartridges 20, the IOL 50 is folded just prior to insertion by manipulation of the cartridge 20 and is engaged by the plunger 16 in a folded condition, as described below. The folded IOL 50 is pushed out of the tip 18 of the injector 10 inserted in the eye through the incision and is spread (unfolded) and placed in the eye.

It is essential for IOLs 50 to be stored unstressed so as not to become permanently deformed over time. Accordingly, IOLs 50 are not held in a folded condition over a long period of time (i.e. in storage).

More recently, disposable, single-use injectors 10 have come preloaded with an IOL 50. Preloaded injectors designed for delivery of hydrophobic IOLs usually incorporate lens storage within the main injector body. Due to its simplicity, this is a more preferable option for a preloaded injector and is possible because hydrophobic IOLs can be stored in a non-hydrated or 'dry' state. Examples of known preloaded systems include four fully preloaded injectors: Isert Acrylat, hydrophobic aspheric; Acrysert Acrylat, hydrophobic aspheric; NX-1 Nex-load Acrylat, hydrophobic aspheric; and KS3-Ai Silicone aspheric (respectively manufactured by Hoya, Alcon, Domilens and STAAR-Domilens).

In contrast to hydrophobic IOLs, hydrophilic IOLs must be stored hydrated, normally completely submerged in a saline solution. As a consequence, semi-preloaded injectors for hydrophilic IOLs, requiring insertion of a cartridge into the injector by the end user, are used for hydrophilic IOLs. The IOL is held within a cartridge submerged in saline during storage, then removed and attached to the main body of an injector (dry) immediately prior to use, much as described above in connection with the early titanium injectors 10. Examples of known semi-preloaded injectors include: Polysert PPS Acrylat, hydrophobic aspheric; XL Stabi Sky Acrylat, Hydrophilic, aspheric; and Slimflex m1.2.3, Acrylat hydrophilic, aspheric (respectively manufactured by Polytech, Zeiss and Technoko).

The clinical argument for preloaded lenses is convincing. Manual loading of IOLs into injectors is usually carried out by the end user (e.g. a nurse or a surgeon), often in low light and under the stress of operating theatre conditions. Since manual insertion of the lens into the cartridge is not necessary with preloaded injectors, there is no additional risk of contamination, no mechanical damage because of contact with the lens by instruments, no 180° upside-down confusion, and no loss of the IOL on the operating table. Injection of the IOL is standardized. The injector systems themselves are all disposable materials; there is absolutely no more need for complicated preparation of the instruments for re-use.

As mentioned above, with some known cartridges 20, the IOL 50 may be held in an unfolded state within the injector 10. Accordingly, when the cartridge 20 is inserted into the injector 10, the IOL remains unfolded. It is only once the IOL is engaged and urged out of the tip 18 of the injector by the plunger 16 that the IOL becomes folded for injection through the incision in the eye.

In some known cartridges, the cartridge is manipulated prior to insertion into the injector in order to fold the IOL within. For example, the currently most common IOL injector cartridge format includes a pair of hinged flaps that, in a first configuration, define a chamber that holds the IOL in an unfolded state. When the flaps are hinged together, the chamber becomes reduced in size, thus folding the IOL within. This is also the case with integral cartridges; the IOL is inserted into a loading bay of the injector (defined within the integral cartridge) at the point of use in an unfolded state and the flaps of the cartridge are then closed to fold the IOL.

SUMMARY OF THE INVENTION

According to the invention, there is provided a cartridge adapted to store and to fold a foldable, implantable medical device, the cartridge comprising:
a. a first portion; and
b. a second portion interengaged with the first portion;
wherein the first and second portions are movable relative to one another from a storage configuration, in which interior surfaces of the first and second portions define a storage chamber for storing the medical device in an unfolded state, to an implanting configuration, in which the interior surfaces of the first and second portions together define a smooth-bored chamber for retaining the medical device in a folded state.

In one embodiment, the first portion comprises at least one plate and at least one adjacent land, and the second portion comprises a land corresponding to the or each of the at least one plates of the first portion and a plate corresponding to the or each of the at least one lands of the first portion. In this embodiment, in the storage configuration, the plates of the first and second portions are interdigitated and interior surfaces thereof define, at least in part, the storage chamber, whereas in the implanting configuration the plates of the first and second portions overlie their respective corresponding lands. At least one of the plates may include a tooth at a distal end, the corresponding land including a detent, the tooth engaging the detent when the first and second portions are in the implanting configuration.

In a first aspect of the invention, the first and second portions are interengaged by a hinge, pivotably moveable relative to one another about the hinge. The first and second portions may each comprise an arcuate segment of the inner surface that, in the implanting configuration, respectively define opposite halves of the smooth-bored chamber; the first portion comprising first and second spaced plates projecting from an upper side of the arcuate segment; and the second portion comprising a third plate projecting centrally from an upper side of the arcuate segment; the third plate of the second portion being disposed between the first and second plates of the first portion.

The first and second portions of the cartridge according to the first aspect may each comprise a flap extending in a radial direction along a line from the hinge. The flaps of the first and second portions may be aligned with one another when the first and second portions are in the implanting configuration.

In a second aspect of the invention, the first and second portions are slidably moveable relative to one another. The first portion and the second portion may be substantially identical, the first portion being rotated 180° relative to the second portion about both a vertical and a horizontal axis. The first and second portions may each comprise:
a. an arcuate segment of the inner surface that, in the implanting configuration, defines half of the smooth-bored chamber;
b. first and second spaced plates projecting from a lower side of the arcuate segment; and
c. a third plate projecting centrally from an upper side of the arcuate segment;
wherein the third plate of the second portion is disposed between the first and second plates of the first portion and vice versa.

In one embodiment, the smooth-bored chamber of the implanting configuration is cylindrical.

In one embodiment, the smooth-bored chamber of the implanting configuration is tapered in the longitudinal direction.

In one embodiment, the cartridge further includes a foldable, implantable medical device. The medical device is an intraocular lens.

Prior art cartridges have suffered from problems of the IOLs catching on the interior surface of the IOL chamber during injection of the IOL into the eye. This can be a problem in that it causes uneven injection forces, giving the surgeon difficulty in controlling the speed of injection. Also, it can cause damage to the delicate optics and haptics, which is clearly undesirable. For example, 'J. M. Schmidbauer, et al. *J. Cataract. Refract. Surg.* 2002; 28 (7)1223-1228' states that optic or haptic damage has previously accounted for over 14% of intraoperative foldable lens explantations. This catching of the IOL during injection may be caused by an irregular interior surface of the IOL chamber. For example, in prior art cartridges having a pair of hinged flaps, a small gap is left in the interior surface of the IOL chamber between the flaps when they are hinged together to an injecting configuration. In other prior arrangements, features may protrude into the IOL chamber. The present invention solves these and other problems by ensuring the provision of a smooth-bored chamber.

According to a third aspect of the invention, there is provided a medical device injector, comprising:
a. a hollow body portion having proximal and distal ends;
b. a loading bay disposed at the distal end of the body portion;
c. a tip portion connected to the distal end of the body portion;
d. a plunger, slidably received in the body portion; and
e. a cartridge according to either of the first and second aspects received in the loading bay.

According to a fourth aspect of the invention, there is provided a method of loading a medical device injector, comprising:
a. removing a cartridge that includes a foldable, implantable medical device from aseptic packaging;
b. moving the first and second portions relative to one another so as to move from the storage configuration into the implanting configuration, thereby folding the medical device; and
c. inserting the cartridge into a loading bay in the injector.

BRIEF DESCRIPTION OF THE DRAWINGS

The invention will be described, by way of example, with reference to the accompanying drawings, in which.

DETAILED DESCRIPTION

General

Figure 1A:
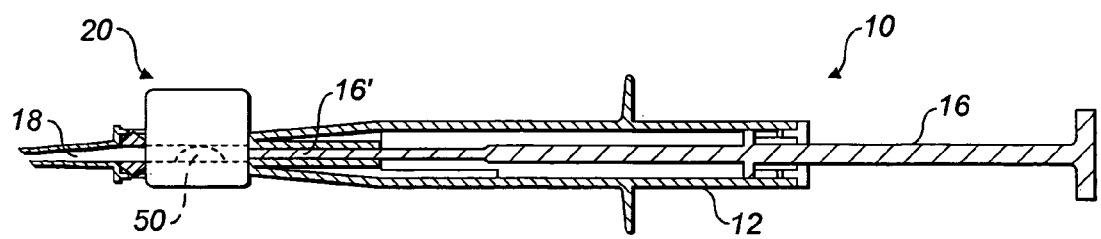
FIG. 1a is a cross-sectional view of a prior art intraocular lens injector having an integral cartridge and shown with a plunger in a rearward position.
Figure 1B:
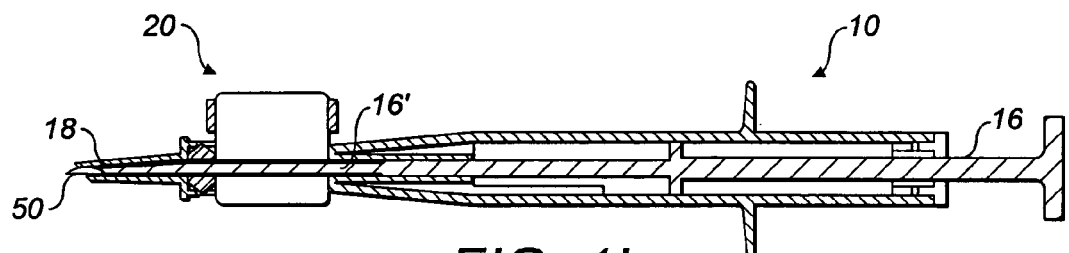
FIG. 1b corresponds to FIG. 1a, but shows the plunger in a forward position, expelling an IOL from the tip.
Figure 2:
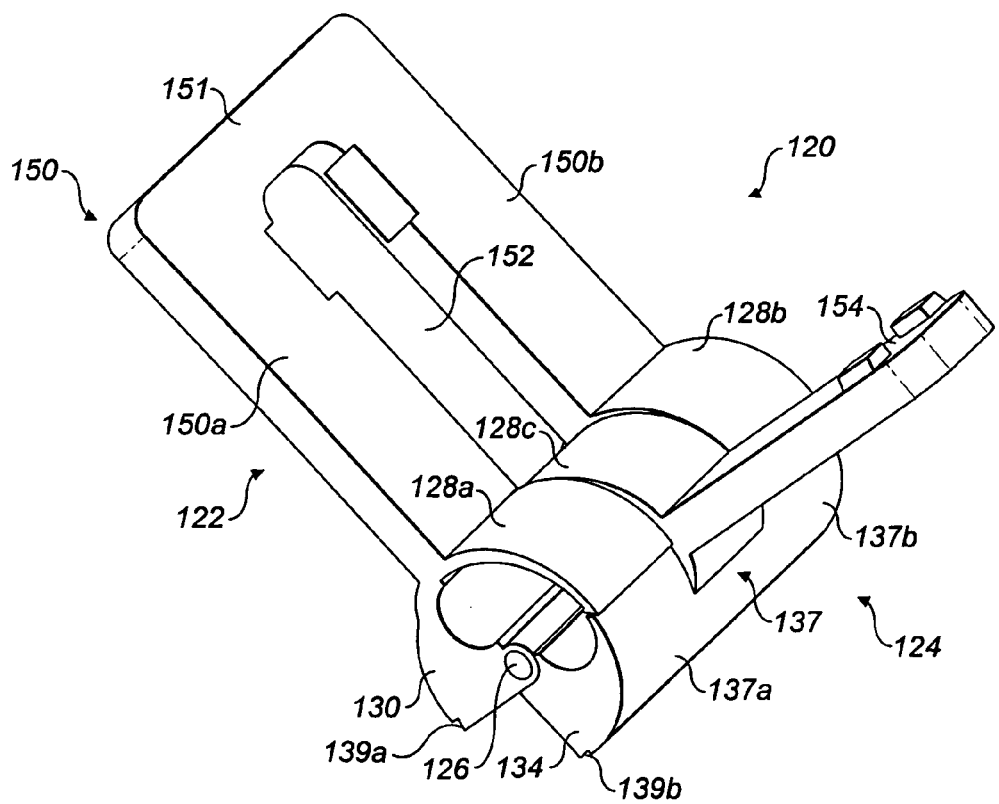
FIG. 2 is a perspective view of a cartridge according to a first aspect of the present invention, shown in an open (storage) configuration.
Figure 3A:
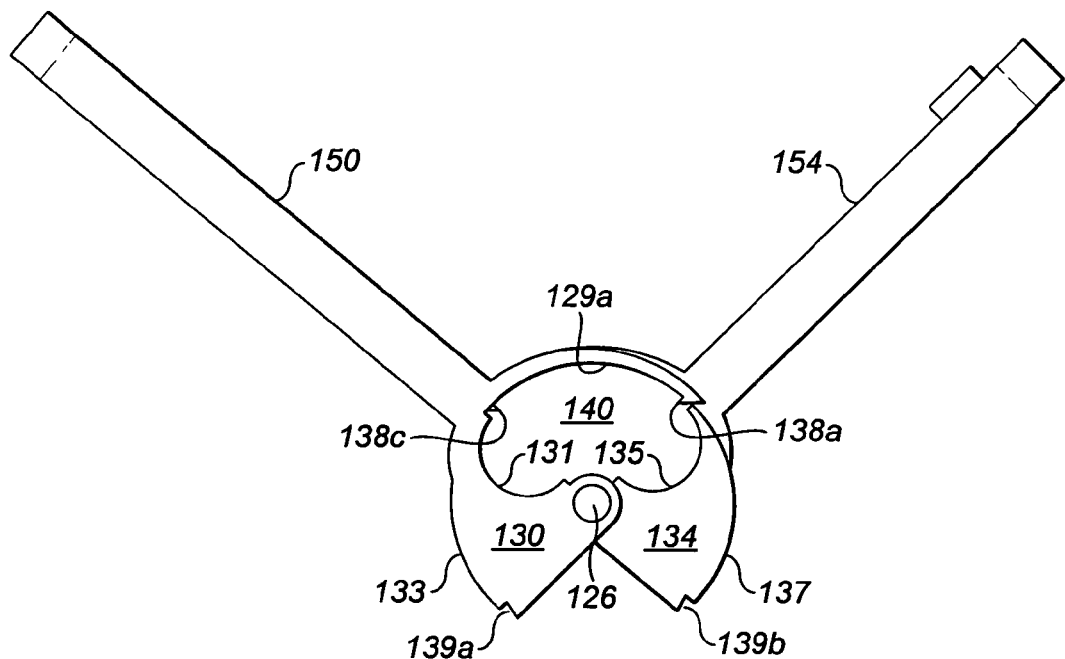
FIG. 3a is an end view of the cartridge of FIG. 2 shown in the open (storage) configuration.
Figure 3B:
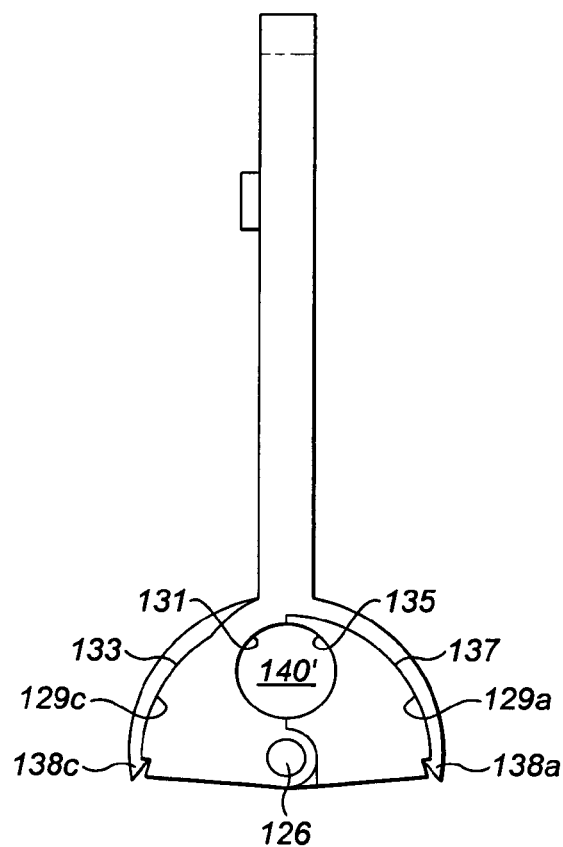
FIG. 3b corresponds to FIG. 3a, but shows the cartridge in a closed (implanting) configuration.
Figure 4:
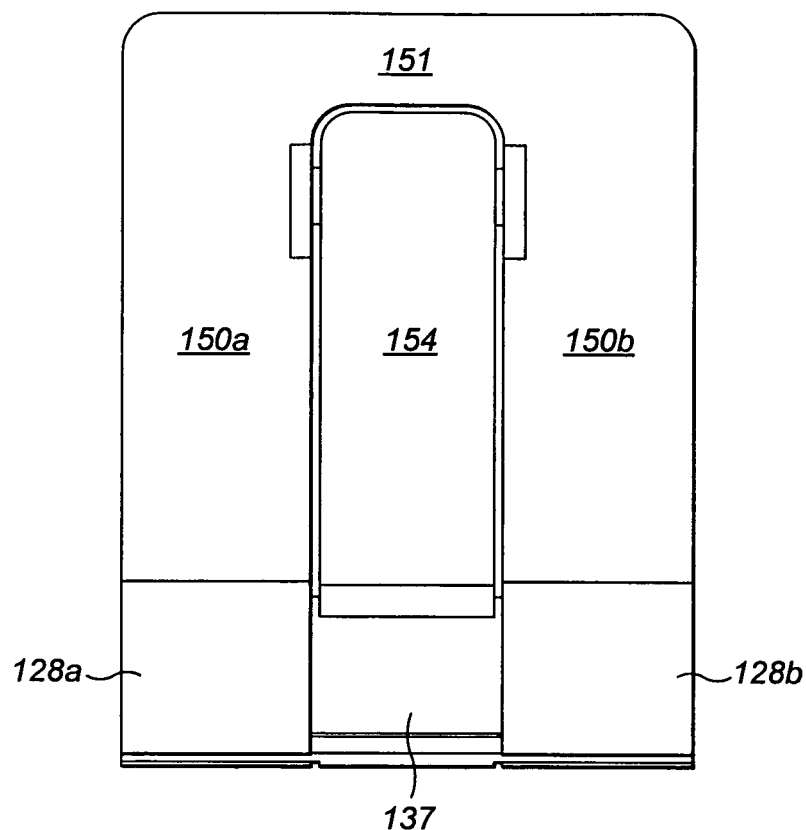
FIG. 4 is a side view of the cartridge of FIG. 3b.
Figure 5:
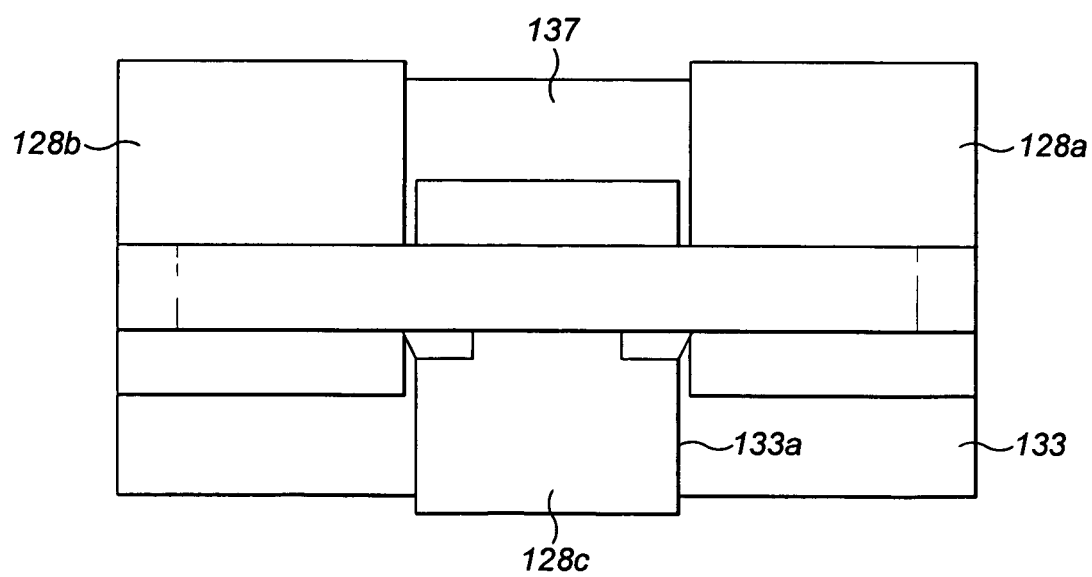
FIG. 5 is a top view of the cartridge of FIG. 3b.
Figure 6A:
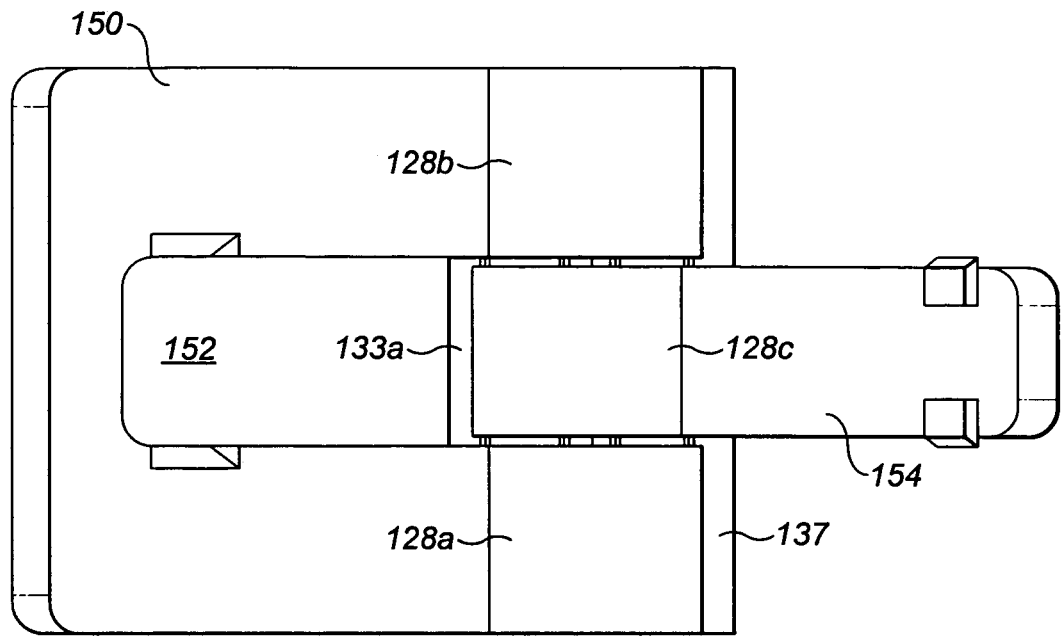
FIG. 6a corresponds to FIG. 5, but shows the cartridge in the open (storage) configuration.
Figure 6B:
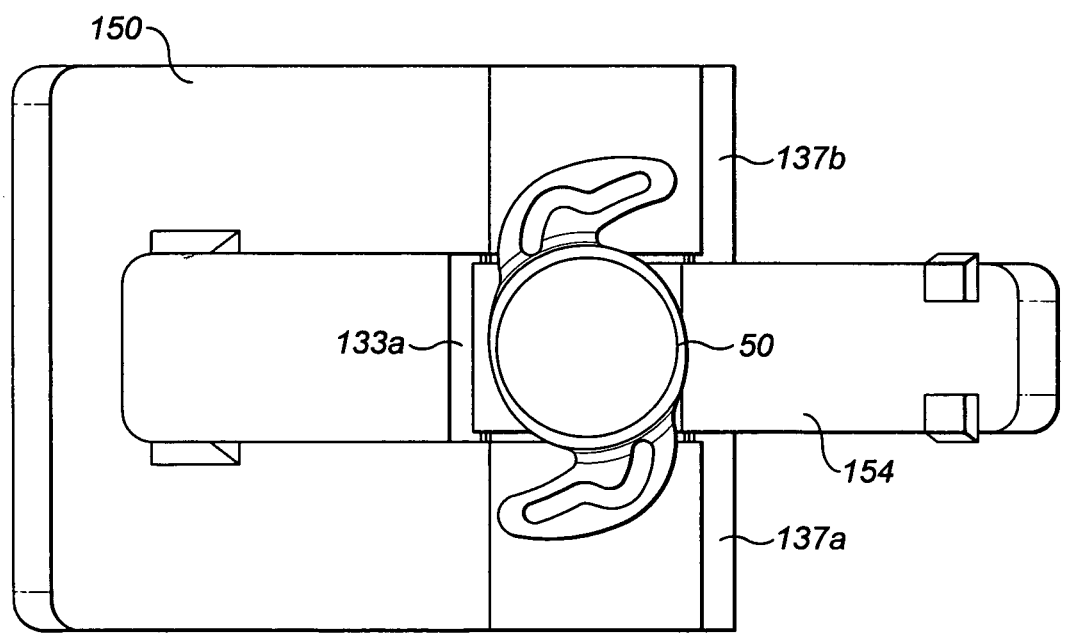
FIG. 6b corresponds to FIG. 6a, but in partial cut-away, showing an IOL in position.

The term "comprising" encompasses "including" as well as "consisting" e.g. a device "comprising" X may consist exclusively of X or may include something additional e.g. X+Y.

The word "substantially" does not exclude "completely". Where necessary, the word "substantially" may be omitted from the definition of the invention.

The terms "top", "bottom", "sides" and other terms describing the orientation of features are not intended to be limiting and are purely included in order to facilitate the description of the relative location of those features in the context of the accompanying drawings. In use, the features may be disposed in other orientations.

Where a particular feature referred to in the following description is accompanied by a reference numeral, it is not necessary that this feature is explicitly illustrated in the Figures. However, where such a feature is not illustrated, the applicant has endeavoured to indicate that the feature is "not shown" in parentheses. Failure to do so should not be considered limiting the scope of invention in any way.

A cartridge 120 according to one embodiment of the first aspect of the invention will be described by reference to FIGS. 2 to 7b. The cartridge 120 comprises a first portion 122 and a second portion 124 interengaged with the first portion by a hinge 126. The first and second portions 122, 124 are thus pivotably moveable relative to one another about the hinge 126 from a storage configuration to an implanting configuration, as explained in greater detail below.

The first portion 122 comprises a first plate 128a at a first end of a longitudinally extending main section 130 and a second plate 128b, spaced from the first plate, at a second, opposite end of the main section 130. The main section 130 has an arcuate interior surface 131 that is semi-circular in cross section. The first and second plates 128a, 128b are both generally arcuate, having interior surfaces 129a, 129b having a radius of curvature centred on the axis of the hinge 126. The first and second plates 128a, 128b project towards the second portion 124 from an upper side of the main section 130, remote from the hinge 126.

The main section 130 has an exterior surface 133 having a radius of curvature centred on the axis of the hinge 126. A central portion of that exterior surface 133 (i.e. the portion adjacent to the space between the first and second plates 128a, 128b) comprises a land 133a.

The first portion 122 includes a first flap 150 that extends outwardly from the upper side of the main section 130 in a radial direction along a line from the hinge 126. The flap comprises a first arm 150a having a proximal end aligned with and extending from the interface between the first plate 128a and the main section 130 and a second arm 150b aligned with and extending from the interface between the second plate 128b and the main section 130. The first and second arms 150a, 150b are interconnected at their distal ends by a longitudinally extending shoulder 151. A space 152 is defined by the spaced first and second arms 150a, 150b and the shoulder 151.

The second portion 124 comprises a longitudinally extending main section 134 with a third plate 128c centrally disposed thereon. The main section 134 has an arcuate interior surface 135 that is semi-circular in cross section. The third plate 128c is, like the first and second plates 128a and 128b of the first portion 122, generally arcuate, and has an interior surface 129c having a radius of curvature centred on the axis of the hinge 126. The third plate 128c projects towards the first portion 122 from an upper side of the main section 134, remote from the hinge 126. More specifically, the third plate 128c projects towards the first land 133a.

The main section 134 of the second portion 124 has an exterior surface 137 having a radius of curvature centred on the axis of the hinge 126. The end portions of that exterior surface 137 (i.e. the portions on either side of the third plate 128c) comprise respective second and third lands 137a, 137b.

The second portion 124 includes a second flap 154 that extends outwardly from the upper side of the main section 134 in a radial direction along a line from the hinge 126. The second flap 154 has a proximal end aligned with and extending from the interface between the third plate 128c and the main section 134.

Figure 7A:
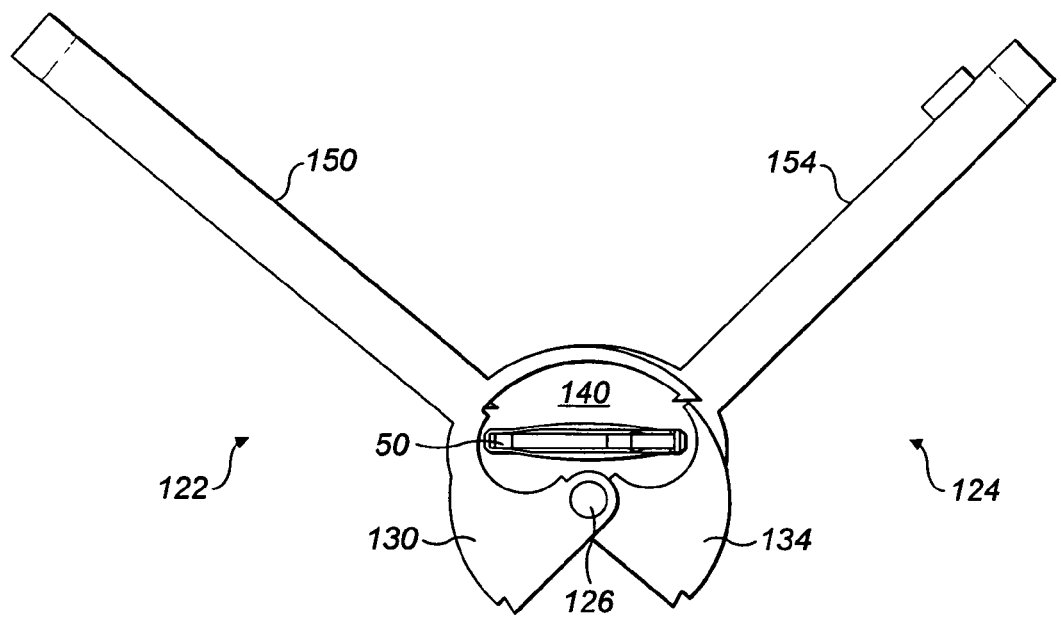
FIG. 7a corresponds to FIG. 3a, but includes an IOL in position.

In the storage configuration, the first and second plates 128a, 128b are interdigitated with the third plate 128c, with substantially no gaps between the adjacent plates. The interior surfaces 129a, 129b, 129c of the respective first, second and third plates 128a, 128b, 128c and the interior surfaces 131, 135 of the respective main portions 130, 134 together define a storage chamber 140 extending parallel to the longitudinal axis of the hinge 126. As best seen in FIG. 7a, the storage chamber 140 is of a shape and configuration suitable for storing an IOL 50 snugly in an unfolded state.

Each of the plates 128a-c includes a tooth 138a-c at a distal end, remote from the corresponding upper ends of the main sections 130, 134. The first and second portions 122, 124 each include a detent groove 139a, 139b running the length of the respective main sections 130, 134 at lower ends of their exterior surfaces 133, 137.

To move the first and second portions 122, 124 from the storage configuration to the implanting configuration, a user squeezes the first and second flaps 150, 154 together. The flaps provide leverage, increasing the moment at the hinge 126. As the flaps 150, 154 are brought together, the plates 128a-c slide over their respective lands, 137a, 137b, 133a, the curvature of the interior surfaces 129a-c of the respective plates 128a-c matching the curvature of the external surfaces of the main sections 130, 134. The third plate 128c slides through the space 152 between the first and second parts 150a, 150b of the first flap 150, whereas the first and second plates 128a, 128b slide past the second flap 154 on respective sides thereof.

More particularly, it is the teeth 138a-c of the respective plates that slide up and over the corresponding lands 137a, 137b, 133a until the teeth have passed the far end of the lands, when the resilient nature of the plates 128a-c urges the teeth back to a non-deflected position, within the respective detent grooves 139a, 139b. This interengagement of the teeth within the corresponding detents is non-reversible and ensures that the first and second portions 122, 124 cannot be returned to the storage configuration. This is to prevent re-use of what is intended to be a single-use cartridge.

When the first and second flaps 150, 154 are aligned with one another, the second flap 154 being received within the space 152 between the first and second arms 150a, 150b of the first flap, the first and second portions 122, 124 are in the implanting configuration.

In the implanting configuration, the semi-circular cross-sectional interior surfaces 131, 135 of the respective main sections 130, 134 of the first and second portions 122, 124 together define a cylindrical, smooth-bored implanting chamber 140' extending parallel to the longitudinal axis of the hinge 126. In this implanting configuration, the first plate 128a overlies the second land 137a, the second plate 128b overlies the third land 137b and the third plate 128c overlies the first land 133a.

A cartridge 220 according to one embodiment of the second aspect of the invention will be described by reference to FIGS. 8a to 11b. The cartridge 220 comprises a first portion 222 and a second portion 224 slidably interengaged with the first portion. The first and second portions 222, 224 are thus slidably moveable relative to one another from a storage configuration to an implanting configuration, as explained in greater detail below.

The first portion 222 comprises a first plate 228a at a first end of a longitudinally extending main section 230 and a second plate 228b, spaced from the first plate, at a second, opposite end of the main section 230. The first and second plates 228a, 228b are both generally planar and project towards the second portion 224 from an upper side of the main section 230. A third plate 228c, which is also generally planar, is centrally disposed on a lower side of the main section 230 and projects towards the second portion 224. The first, second and third plates 228a-c each have interior surfaces 227. The main section 230 has an arcuate interior surface 231 that is semi-circular in cross section.

The main section 230 has a substantially flat top surface 233. A central portion of that top surface 233 (i.e. the portion adjacent to the space between the first and second plates 228a, 228b) comprises a first land 233a. The first land 233a is a shallow wedge shape which increases in height from level with the top surface 233 at an end closest to the arcuate interior surface 231.

The main section 230 also has a substantially flat bottom surface 237. Side edge portions of that bottom surface 237 (i.e. the portions in line with the first and second plates 228a, 228b) comprise respective second and third lands 237a, 237b.

The second portion 224 is identical to the first portion 222, but rotated 180° relative to the first portion about both a vertical and a horizontal axis. The second portion 224 thus comprises a fourth plate 228d centrally disposed on a longitudinally extending main section 234. The fourth plate 228d is generally planar and projects towards the first portion 222 from an upper side of the main section 234. The second portion 224 further comprises a fifth plate 228e at a first end of the longitudinally extending main section 234 and a sixth plate 228f, spaced from the fourth plate, at a second, opposite end of the main section 234. The fifth and sixth plates 228e, 228f are both generally planar and project towards the first portion 222 from a lower side of the main section 234. The fourth, fifth and sixth plates 228d-f each have interior surfaces 229. The main section 230 has an arcuate interior surface 231 that is semi-circular in cross section.

The main section 234 of the second portion 224 has a substantially flat top surface 239. Side edge portions of that top surface 239 (i.e. the portions in line with the fifth and sixth plates 228e, 228f) comprise respective fourth and fifth lands 239a, 239b.

The main section 234 also has a substantially flat bottom surface 241. A central portion of that bottom surface 241 (i.e. the portion adjacent to the space between the fifth and sixth plates 228e, 228f) comprises a sixth land 241a. The sixth land 241a is a shallow wedge shape which increases in height from level with the bottom surface 241 at an end closest to the arcuate interior surface 235.

Each of the plates 228a-f includes a tooth 238a-f at a distal end, remote from the corresponding main sections 230, 234.

In the storage configuration, the first and second plates 228a, 228b are interdigitated with the fourth plate 228d, with substantially no gaps between the adjacent plates. Likewise, the fifth and sixth plates 228e, 228f are interdigitated with the third plate 228c, with substantially no gaps between the adjacent plates. The teeth 238a-f prevent the separation of the first and second portions 222, 224 beyond a desired point by butting engagement against respective shoulder portions 242-245 on the main sections 230, 234.

Figure 10A:
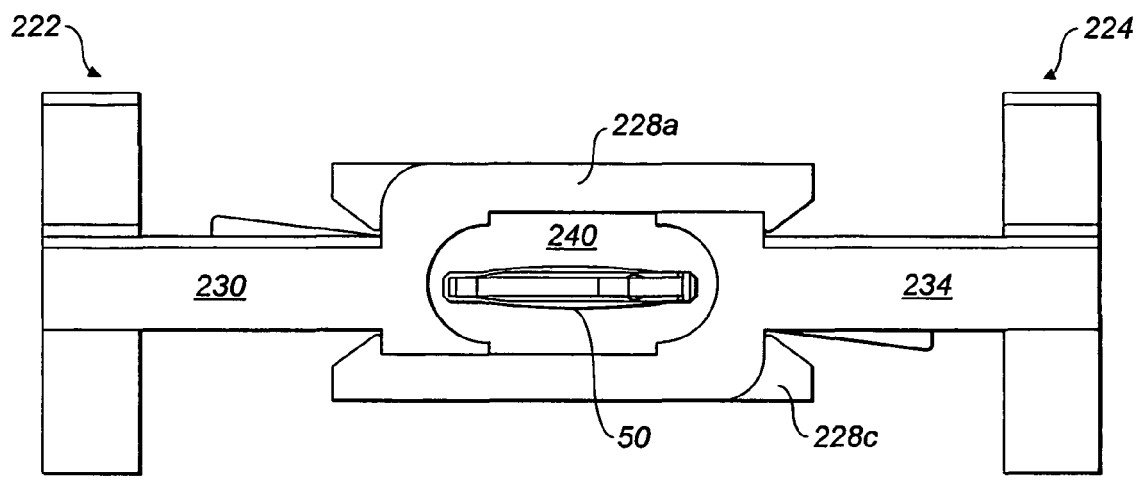
FIG. 10a is an end view (on 'A' of FIG. 8b) of the cartridge of FIG. 8 shown in the open (storage) configuration and including an IOL in position.

The interior surfaces 227, 229 of the respective plates 228a-f and the interior surfaces 231, 235 of the respective main portions 230, 234 together define a storage chamber 240. As best seen in FIG. 10a, the storage chamber 140 is of a shape and configuration suitable for storing an IOL 50 snugly in an unfolded state.

To move the first and second portions 222, 224 from the storage configuration to the implanting configuration, a user squeezes the first and second portions together. As the first and second portions 222, 224 are brought together, the plates 228a-f slide over their respective lands, 233a, 237a, 237b, 239a, 239b, 241a. The fourth plate 228d slides through the space between the first and second plates 228a, 228b and up and over the first land 233a. Likewise, the third plate 228c slides through the space between the fifth and sixth plates 228e, 228f and up and over the sixth land 241a. More particularly, it is the teeth 238d, 238c of the respective fourth and third plates that slide up and over the corresponding first and sixth lands 233a, 241a until the teeth have passed the far end of the lands, when the resilient nature of the plates 228d, 228c urges the teeth back to a non-deflected position, abutting an end face 233a', 241a' of the respective lands. In this manner, the relative movement to the implanting configuration is non-reversible and ensures that the first and second portions 222, 224 cannot be returned to the storage configuration. This is to prevent re-use of what is intended to be a single-use cartridge.

In the implanting configuration, the semi-circular cross-sectional interior surfaces 231, 235 of the respective main sections 230, 234 of the first and second portions 222, 224 together define a cylindrical, smooth-bored implanting chamber 240'. In this implanting configuration, the first plate 228a overlies the fourth land 239a, the second plate 228b overlies the fifth land 239b, the third plate 228c overlies the first land 233a, the fourth plate 228d overlies the sixth land 241a, the fifth plate 228e overlies the second land 237a and the sixth plate 228f overlies the third land 237b.

Figure 7B:
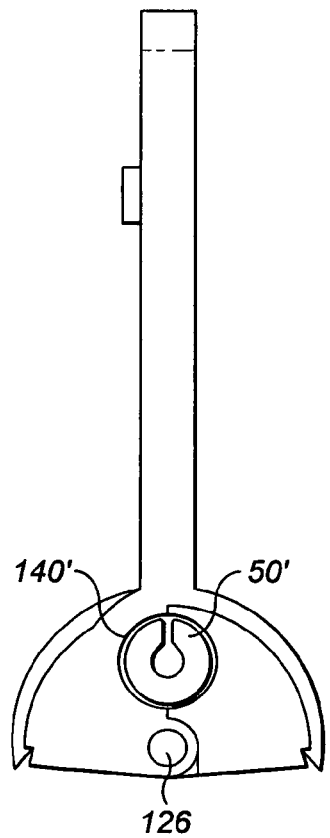
FIG. 7b corresponds to FIG. 3b, but includes a folded IOL in position.
Figure 8A:
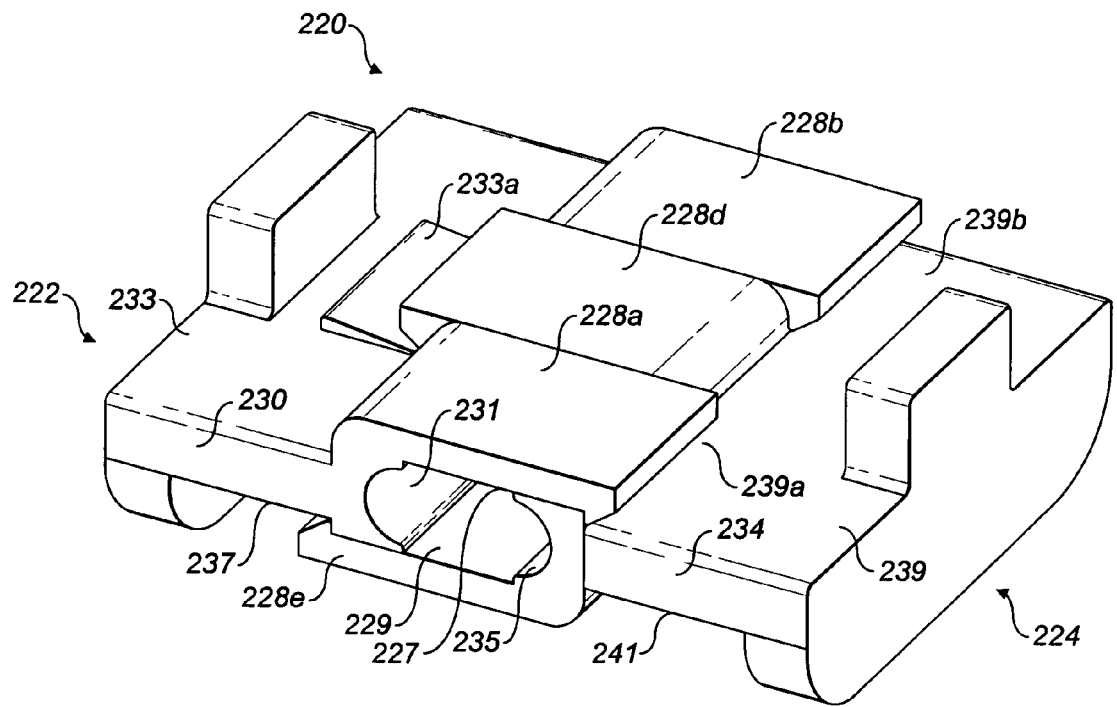
FIG. 8a is a perspective view of a cartridge according to a second aspect of the present invention, shown in an open (storage) configuration.
Figure 8B:
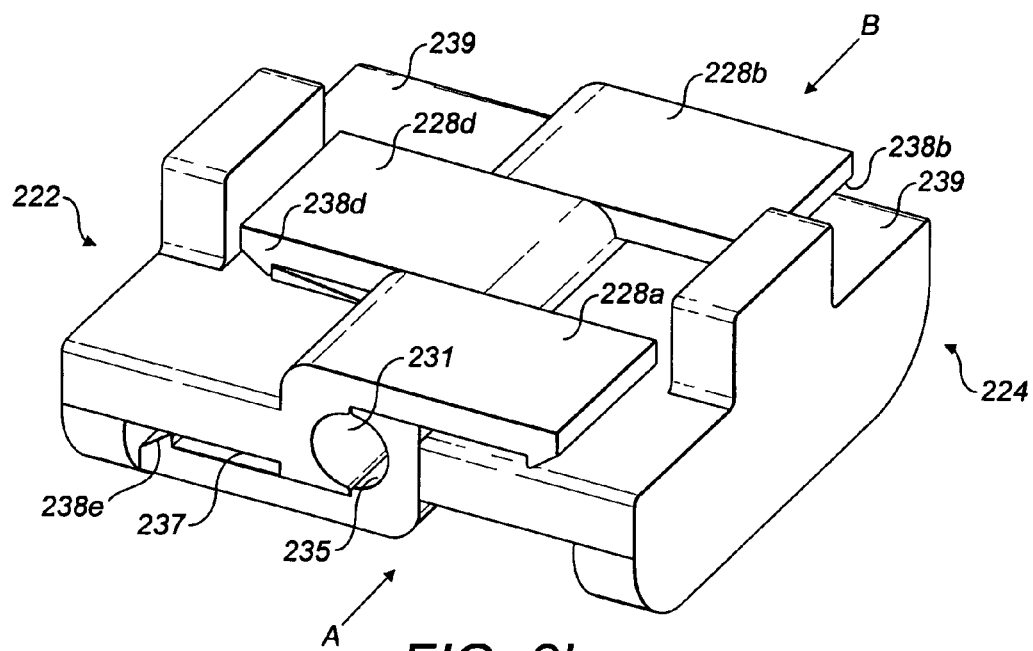
FIG. 8b corresponds to FIG. 8a, but shows the cartridge in a closed (implanting) configuration.
Figure 9A:
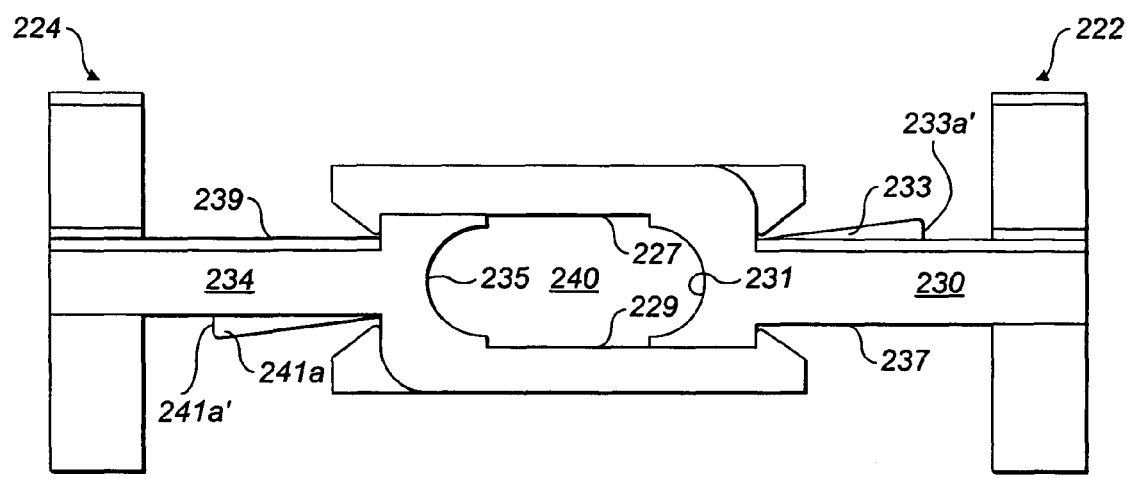
FIG. 9a is an end view (on 'B' of FIG. 8b) of the cartridge of FIG. 8 shown in the open (storage) configuration.
Figure 9B:
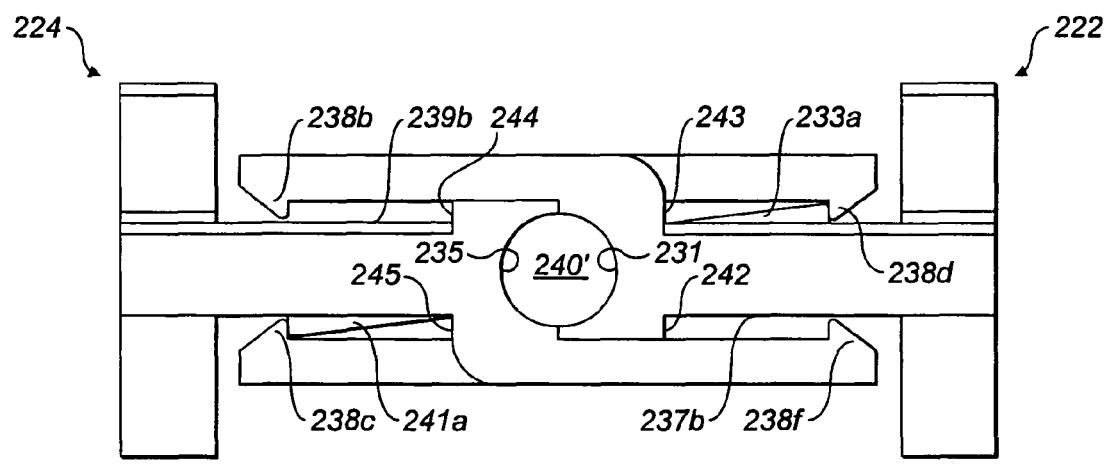
FIG. 9b corresponds to FIG. 9a, but shows the cartridge in the closed (implanting) configuration.
Figure 10B:
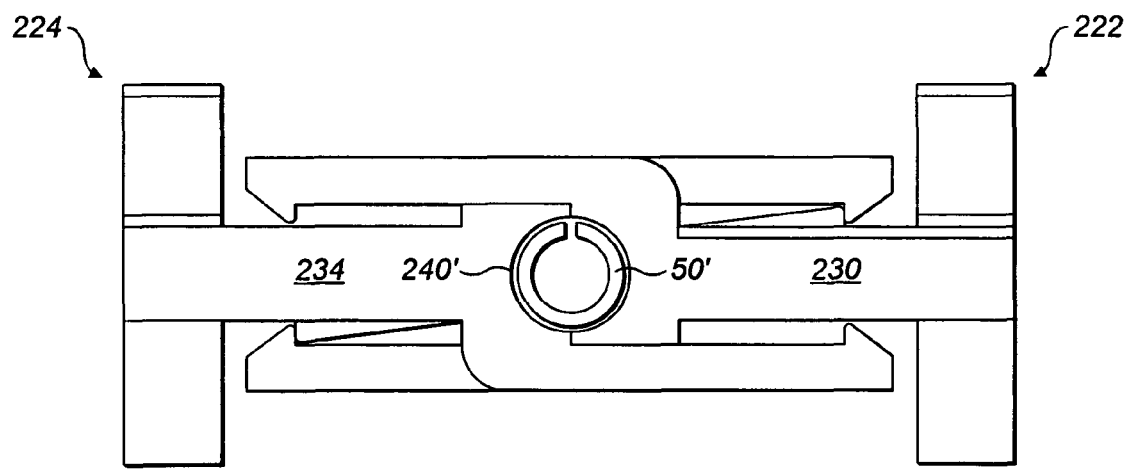
FIG. 10b corresponds to FIG. 9b, but includes a folded IOL in position.
Figure 11A:
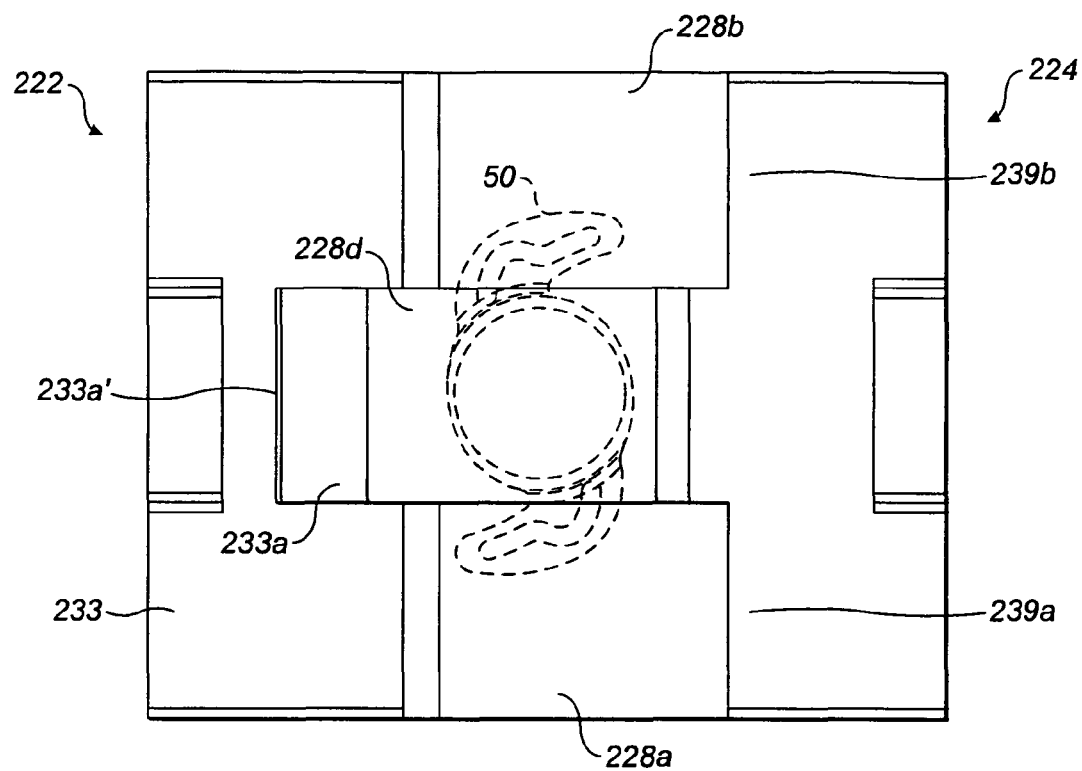
FIG. 11a is a top view of the cartridge according to the second aspect of the invention in the closed (implanting) configuration and showing in phantom an IOL in position.
Figure 11B:
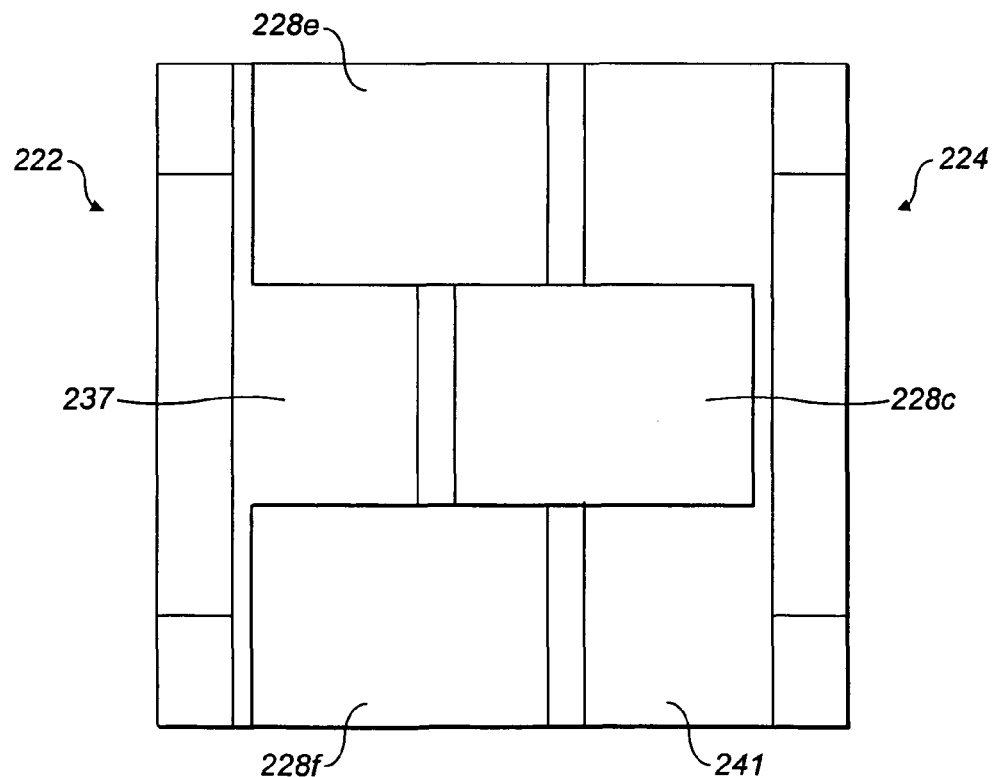
FIG. 11b corresponds to FIG. 11a, but shows the cartridge in a closed (implanting) configuration and from below.

With the cartridge of either the first or the second aspects, during the transition from the storage configuration to the implanting configuration, the IOL 50 is folded to a folded state 50', which can be seen most clearly in FIGS. 7b and 10b.

A cartridge 120, 220 according to either of the first and second aspects of the invention may be stored, with an IOL 50 in situ, in a storage configuration within aseptic packaging (not shown). The packaging may include a feature to retain the IOL 50 in place within the cartridge 120, 220. At the point of use, an end user would: remove the cartridge from the aseptic packaging; move the first and second portions 122, 124; 222, 224 relative to one another so as to move from the storage configuration into the implanting configuration, thereby folding the IOL 50; and insert the cartridge 120, 220 into a loading bay in an injector. Alternatively, the step of moving the cartridge 120, 220 from the storage configuration into the implanting configuration could take place prior to the removing step, the IOL 50 thus being folded whilst still in the packaging.

At no stage in the process is the IOL 50 handled by the end user; the cartridge 120, 220 fully encloses the IOL at all stages of storage and implantation, right up to the point when the IOL is expelled from the injector into the eye. This therefore greatly reduces the risks of contamination and/or placement errors.

Because of the smooth bore of the implanting chamber 140', 240', there are no irregular surfaces on which the folded IOL 50' or the injector plunger 16 might catch during expulsion of the IOL from the chamber, so injection of the folded IOL 50' is smooth and controlled, reducing risk to the patient and improving ease of use for the surgeon.

Although the cartridge 120, 220 and associated injector have been described in the context of the storage and injection of intraocular lenses 50, and especially hydrophilic IOLs, the skilled person would appreciate that the invention has further application and may equally be applied to the storage and implantation of non-hydrophilic IOLs (which can be stored dry for up to five years) or other foldable medical devices, with suitable adaptation, where necessary, of the shape and configuration of the storage and implantation chambers 140, 140'; 240, 240' and of the injector.

Rather than being circular in cross section, the implanting chamber 140', 240' could be of any appropriate cross sectional shape, such as oval, square or octagonal. Moreover, it is not necessary for the sides of the bore to be parallel. Instead, the bore could be tapered, narrowing in the longitudinal direction. Also, the cross sectional shape of the bore could change along its length.

The cartridge 120, 220 could be made of multiple materials so as to achieve optimum properties and/or cost. For example, the interior surfaces 131, 135; 231, 235 defining the bore of the implanting chamber 140', 240' could be made of a highly lubricious material whilst the rest of the cartridge is made of standard grade plastics. Also, the plates 128a-c; 228a-f could be made of a material that has particularly good properties for resilience, for example.

The entire cartridge 120, 220 could be coated in a lubricious coating or could contain a lubricious agent to reduce friction thereby facilitating ejection of the IOL 50 from the cartridge 120, 220.

Alternatively or additionally, the injector may contain a lubricious sleeve (not shown) to be pushed over the folded IOL 50' by the injector plunger after the cartridge has been inserted into the loading bay of the injector.

Rather than being a separate cartridge and injector combination, the cartridge could be incorporated into and be integral with the injector. Alternatively, the cartridge may have an integral nozzle section, for use with an injector having no nozzle or tip section.

Instead of there being the specific number of plates and corresponding lands as described in detail above, the cartridge of either aspect of the invention may have either more or fewer plates and corresponding lands.

Instead of the entire exterior surface of the main sections 130, 134 of the cartridge 120 of the first aspect having a curvature matching that of the plates, it is only necessary for the portions that are slid over by the plates 128a-c (i.e. the lands 137a, 137b, 133a) to have a matching profile.

Although the first flap 150 is described as having first and second arms 150a, 150b connected by a shoulder 151, it will be appreciated that the shoulder 151 could be omitted. In fact, just a single arm 150a could be used in conjunction with the second flap 154. If no flaps were provided, the user would still be able to move the first and second portions 122, 124 together to the implanting configuration, but with greater effort.

The first and second portions 222, 224 of the cartridge of the second aspect of the invention do not have to be identical, although this facilitates manufacture.

The invention claimed is:

1. A cartridge adapted to store and to fold a foldable, implantable medical device, the cartridge comprising:
   a. a first portion; and
   b. a second portion interengaged with the first portion;
   wherein the first and second portions are movable relative to one another from a storage configuration, in which interior surfaces of the first and second portions define a storage chamber for storing the medical device in an unfolded state, to an implanting configuration, in which the interior surfaces of the first and second portions together define smooth-bored chamber for retaining the medical device in a folded state;
   wherein the first and second portions are interengaged by a hinge, pivotably moveable relative to one another about the hinge; and
   wherein the first and second portions each comprise an arcuate segment of the inner surface that, in the implanting configuration, respectively define opposite halves of the smooth-bored chamber; wherein the first portion comprises first and second spaced plates projecting from an upper side of the arcuate segment; and wherein the second portion comprises a third plate projecting centrally from an upper side of the arcuate segment; wherein the third plate of the second portion is disposed between the first and second plates of the first portion.

2. The cartridge according to claim 1, wherein the first portion comprises at least one plate and at least one adjacent land, wherein the second portion comprises a land corresponding to the or each of the at least one plates of the first portion and a plate corresponding to the or each of the at least one lands of the first portion, wherein in the storage configuration the plates of the first and second portions are interdigitated and interior surfaces thereof define, at least in part, the storage chamber, and wherein in the implanting configuration the plates of the first and second portions overlie their respective corresponding lands.

3. The cartridge according to claim 2, wherein at least one of the plates includes a tooth at a distal end and wherein the corresponding land includes a detent, the tooth engaging the detent when the first and second portions are in the implanting configuration.

4. The cartridge according to claim 1, wherein the first and second portions each comprise a flap extending in a radial direction along a line from the hinge.

5. The cartridge according to claim 4, wherein the flaps of the first and second portions are aligned with one another when the first and second portions are in the implanting configuration.

6. The cartridge of claim 1, wherein the cartridge is received in a loading bay of a medical device injector, further wherein the medical device injector includes:
 a. a hollow body portion having proximal and distal ends;
 b. the loading bay disposed at the distal end of the body portion;
 c. a tip portion connected to the distal end of the body portion; and
 d. a plunger, slidably received in the body portion.

\* \* \* \* \*